US00PP24446P2

(12) United States Plant Patent
Marcum

(10) Patent No.: US PP24,446 P2
(45) Date of Patent: May 13, 2014

(54) ***IPOMOEA* PLANT NAMED 'KELLY RAY'**

(50) Latin Name: *Ipomoea batatas*
Varietal Denomination: Kelly Ray

(75) Inventor: Kelly R. Marcum, Oklahoma City, OK (US)

(73) Assignee: Marcums Nursery, Oklahoma City, OK (US)

( * ) Notice: Subject to any disclaimer, the term of this patent is extended or adjusted under 35 U.S.C. 154(b) by 194 days.

(21) Appl. No.: 13/373,991

(22) Filed: Dec. 7, 2011

(51) Int. Cl.
*A01H 5/00* (2006.01)

(52) U.S. Cl.
USPC ..... Plt./258; Plt./226

(58) Field of Classification Search
USPC ..... Plt./258, 226
See application file for complete search history.

(56) References Cited

PUBLICATIONS

"Bloomin' News—Oklahoma County Master Gardeners, Jul. 2012" newsletter (2 pages total).*

* cited by examiner

*Primary Examiner* — Susan McCormick Ewoldt
(74) *Attorney, Agent, or Firm* — Penny J. Aguirre

(57) ABSTRACT

A new cultivar of hybrid *Ipomoea* named 'Kelly Ray', characterized by its unique foliage with cordate shaped leaves that are irregularly mottled with dark purple and lime green and occasionally divided with one half of the leaf purple and one half of the leaf lime green.

2 Drawing Sheets

Botanical classification: *Ipomoea batatas*.
Cultivar designation: 'Kelly Ray'.

BACKGROUND OF THE INVENTION

The present invention relates to a new and distinct cultivar of *Ipomoea batatus* named 'Kelly Ray' and is hereinafter referred to by its cultivar name 'Kelly Ray'.

The Inventor discovered the new cultivar, 'Kelly Ray', as a naturally occurring chimeral mutation of 'Ace of Spades' (not patented) that was growing in a flat at his nursery in Oklahoma City, Okla. in May 2009.

Asexual reproduction of the new cultivar was first accomplished by terminal stem cutting in Oklahoma City, Okla. in June of 2009. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Kelly Ray' as a new and unique cultivar of *Ipomoea*.

1. 'Kelly Ray' exhibits unique foliage with leaves that are irregularly mottled with dark purple and lime green and occasionally divided with one half of the leaf purple and one half of the leaf lime green.
2. 'Kelly Ray' exhibits leaves that are cordate in shape.

'Kelly Ray' can be compared to its parent plant 'Ace of Spades'. 'Ace of Spades' differs from 'Kelly Ray' in having foliage that is dark purple in color with very rare small spots of lime green. 'Kelly Ray' has foliage that is marbled with both colors. 'Kelly Ray' can also be most closely compared to the cultivars 'Emerald Green' (U.S. Plant Pat. No. 18,307) and 'Pink Frost' (not patented). Both cultivars are similar to 'Kelly Ray' in having variegated to mottled foliage, however they differ in foliage coloration. 'Emerald Green' differs from 'Kelly Ray' in having foliage that is yellow-green and dark green. 'Pink Frost' differs 'Kelly Ray' in having foliage that is white, green, and pink in color.

BRIEF DESCRIPTION OF THE DRAWING

The accompanying colored photographs illustrate the overall appearance and distinct characteristics of the new *Ipomoea*. The photographs were taken of plants about 3 months in age as grown in 4-inch containers under greenhouse conditions in Oklahoma City, Okla.

The photographs in FIG. 1 provide close-up views of young foliage of 'Kelly Ray'.

Figure 1:
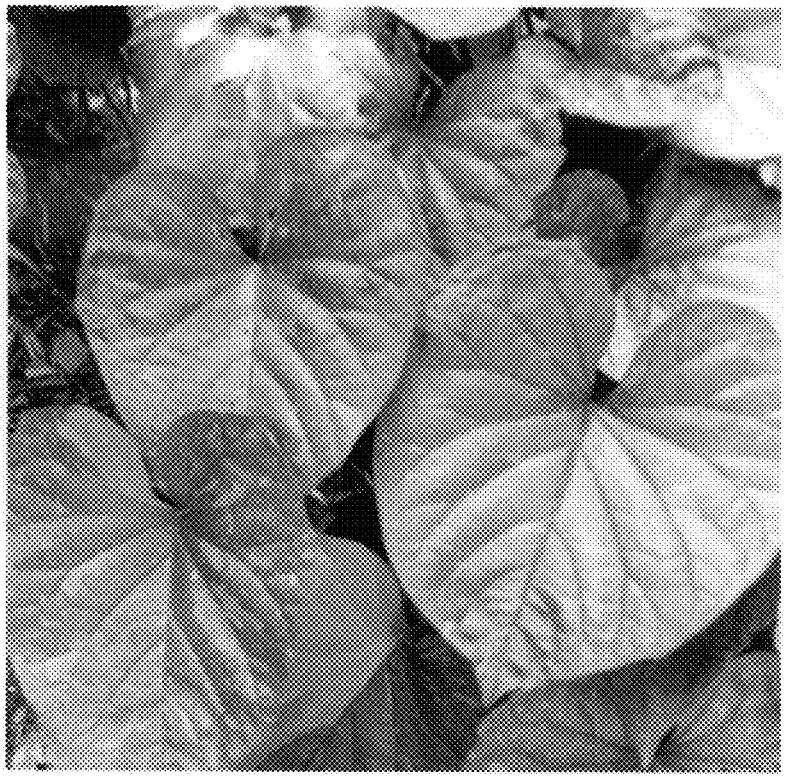
Figure 2:
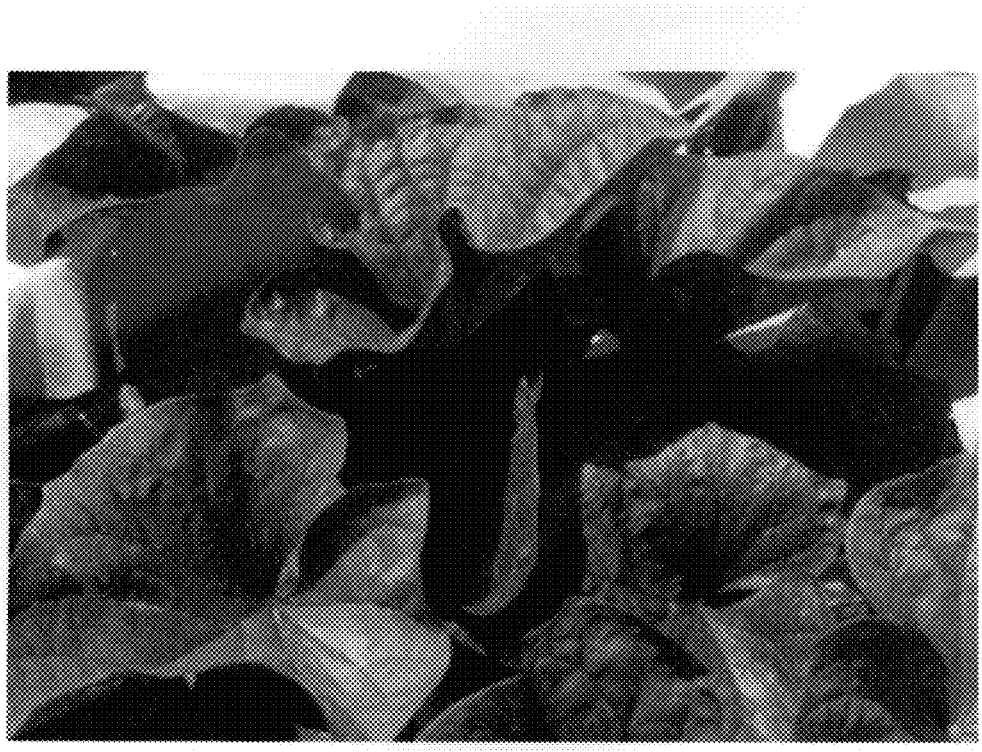

The photographs in FIG. 2 provide close-up views of mature foliage of 'Kelly Ray' when grown under high light and high temperatures.

The colors in the photographs are as close as possible with the digital photography techniques available, the color values cited in the detailed botanical description accurately describe the colors of the new *Ipomoea*.

DETAILED BOTANICAL DESCRIPTION OF THE PLANT

The following is a detailed description of 3 month-old plants of the new cultivar as grown under greenhouse conditions in 1-quart containers in Oklahoma City, Okla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Annual.

*Plant habit.*—Bushy, upright, and mounded.

*Height and spread.*—Reaches a height of 20 cm in height and about 20 cm in width in a 1-quart container.

*Temperature tolerance.*—At least tolerant 5° C. to 35° C.

*Diseases and pests.*—Disease free in the conditions tested, no susceptibility or resistance to pests has been observed.

*Roots.*—Fleshy.

*Tubers.*—Tubers have not be observed to be formed on the new cultivar under the conditions of cultivation used to date.

*Propagation.*—Terminal stem cuttings.

*Growth rate.*—Vigorous.

Stem description:

*Shape.*—Oval.

*Stem color.*—N79A maturing to N92A.

*Stem size.*—An average of 5 mm in diameter and 11 cm in length.

*Stem strength.*—Strong.

*Stem surface.*—Slightly ridged and sparsely covered with hairs.

*Stem number.*—Average of 4 in a 1-quart container.

*Internode length.*—Average of 1.5 cm in length.

*Branching habit.*—Basal branches from base.

Foliage description:

*Leaf shape.*—Cordate.

*Leaf division.*—Simple.

*Leaf base.*—Cordate.

*Leaf apex.*—Broadly acute to cuspidate.

*Leaf venation.*—Palmate, color on upper and lower surface matches leaf color.

*Leaf margins.*—Entire with occasional slight indentations and outward notches.

*Leaf attachment.*—Petiolate.

*Leaf arrangement.*—Alternate.

*Leaf orientation.*—Typically nearly horizontal to petiole.

*Leaf surface.*—Young leaves upper and lower surface; glabrous, satiny and slightly raised between veins on upper surface.

*Leaf color.*—Newly emerging upper and lower surface; 144A, Young upper surface; variable mottling of N77A, 144A and 144B, young lower surface; a mottling of N79B and 138B, mature upper surface; a mottling of N92A and 137C, mature lower surface; a mottling of N79B and 137D, the mature coloration is more intense when grown in high light and high temperatures.

*Leaf size.*—Average of 5.5 cm in length and 7.5 cm in width.

*Petioles.*—Round in shape with a flattened side, average of 7.5 cm in length and 2.5 mm in width, color 59A with very slight striations of 144A, surface is glabrous.

Flower description: Flowering has not been observed for the new *Ipomoea* under the conditions grown. The new cultivar is grown as a foliage plant and has been grown under conditions that are conducive to flower production.

It is claimed:

1. A new and distinct cultivar of hybrid *Ipomoea* plant named 'Kelly Ray' as herein illustrated and described.

* * * * *